(12) United States Patent
Zepf (10) Patent No.: US 7,318,725 B2
(45) Date of Patent: Jan. 15, 2008

(54) DENTAL PLIERS

(75) Inventor: Helmut Zepf, Seitingen-Oberflacht (DE)

(73) Assignee: Helmut Zepf Medizintechnik GmbH, Seitingen-Oberflacht (DE)

( * ) Notice: Subject to any disclaimer, the term of this patent is extended or adjusted under 35 U.S.C. 154(b) by 0 days.

(21) Appl. No.: 11/059,591

(22) Filed: Feb. 16, 2005

(65) Prior Publication Data

US 2005/0186536 A1 Aug. 25, 2005

(30) Foreign Application Priority Data

Feb. 19, 2004 (DE) .................. 20 2004 002 560 U (51) Int. Cl.
*A61C 3/14* (2006.01)
(52) U.S. Cl. .................. 433/159; 81/416; 606/208
(58) Field of Classification Search ................ 433/169, 433/159, 4; 81/416, 415; 606/205, 208
See application file for complete search history.

(56) References Cited

U.S. PATENT DOCUMENTS

| | | | | | |
|---|---|---|---|---|---|
| 918,672 | A | * | 4/1909 | Hansen | 7/130 |
| 1,159,621 | A | * | 11/1915 | Thomson | 81/416 |
| 2,632,661 | A | * | 3/1953 | Cristofv | 403/119 |
| 3,735,763 | A | | 5/1973 | Shannon et al. | |
| 3,903,725 | A | * | 9/1975 | Rommel | 72/409.09 |
| 3,982,450 | A | * | 9/1976 | Marsh | 81/416 |
| 4,662,372 | A | | 5/1987 | Sharkany et al. | |
| 5,197,879 | A | * | 3/1993 | Fowler et al. | 433/159 |
| 5,232,360 | A | * | 8/1993 | Ingels | 433/4 |
| 5,752,419 | A | * | 5/1998 | Liou | 81/416 |
| 6,000,941 | A | * | 12/1999 | Ingels | 433/159 |
| 6,370,991 | B1 | * | 4/2002 | Hsieh | 81/427.5 |

| | | | | |
|---|---|---|---|---|
| 2004/0166475 | A1 | * | 8/2004 | Nikolov ...................... 433/159 |

FOREIGN PATENT DOCUMENTS

| | | |
|---|---|---|
| DE | 743853 C | 9/1909 |
| FR | 401954 A | 1/1944 |

\* cited by examiner

*Primary Examiner*—Ralph A. Lewis
(74) *Attorney, Agent, or Firm*—Stephan A. Pendorf; Peter A. Chiabotti; Akerman Senterfitt (57) ABSTRACT

Dental pliers with two pliers parts, each respectively comprising one jaw of a pliers mouth and one lever arm of a pliers grip, the pliers parts pivotably connected with each other via a linkage. The linkage includes a cylindrical journal (26) on the first pliers part (12) coaxial to the pivot axis, which engages in a cylindrical bore (32) on the other pliers part (10) coaxial to the pivot axis having the same diameter, and is rotatable in this bore (32) about the pivot axis. The journal (26) and the bore (32) are axially located form-fittingly via at least one circumferential tab (28) and one circumferential groove (34). The at least one circumferential tab (28) extends only over a partial angular area of the circumference. At least one entry segment (36) corresponding to the cross-sectional shape of the circumferential tab (28) leads axially to the circumferential groove (34). The at least one circumferential tab (28) and the at least one entry segment (36) are so oriented in their angular orientation in the respective linkage area (22) or as the case may be (24), that these come into registry with each other in the open or spread position of the pliers parts (10, 12), and the at least one circumferential tab (28) can be introduced into the circumferential groove (34) through the entry segment (36) or as the case may be removed therefrom, while in the other spread positions of the pliers parts (10, 12) the at least one circumferential tab (28) engages in the circumferential groove (34) and is held form-fittingly axially therein.

20 Claims, 7 Drawing Sheets

DENTAL PLIERS

BACKGROUND OF THE INVENTION

1. Field of the Invention

The invention concerns dental pliers, in particular extraction pliers.

2. Related Art of the Invention

Pliers in general, and dental pliers in particular, such as extraction pliers, are comprised of two pliers parts, which respectively include one jaw and one lever arm. The pliers parts are connected pivotably with each other via a linkage, also referred to as a bolt or pivot pin. The jaws of the pliers form the pliers mouth, while the lever arms form the pliers grip. In the known pliers the linkage is a flush linkage, in which the two pliers parts are laid on top of each other and connected, or a sandwiched linkage, in which the one pliers part is introduced into a recess machined into the other pliers part and connected therewith, or as an insertion linkage, in which the one pliers parts is introduced through an opening in the other pliers part. The two pliers parts are riveted to each other at the pivot axes, so that the two pliers parts are inseparatably connected to each other. It is likewise known to connect the two pliers parts using a screw located in the pivot axes. In this case a separation of the pliers parts is possible, which is advantageous in particular for cleaning, disinfection and, in certain cases, sterilization. The disassembly of the pliers is however laborious and time consuming.

SUMMARY OF THE INVENTION

The invention is concerned with the task of providing dental pliers which are easy to assemble and to again reassemble.

The task is inventively solved by dental pliers with first and second pliers parts, each respectively comprising one jaw of a pliers mouth and one lever arm of a pliers grip, which pliers parts are connected with each other pivotably about a pivot axis via a linkage comprising a cylindrical journal (26) on the first pliers part (12) coaxial to the pivot axis, a cylindrical bore (32) in the second pliers part (10) coaxial to the pivot axis, receiving and having the same diameter as the cylindrical journal (26), the received cylindrical journal (26) rotatable in this bore (32) about the pivot axis, wherein the journal (26) and the bore (32) are axially located form-fittingly via at least one circumferential tab (28) and one circumferential groove (34), wherein the at least one circumferential tab (28) extends only over a partial angular area of the circumference, wherein at least one entry segment (36) is provided having the cross-sectional shape of the circumferential tab (28) and leading axially to the circumferential groove (34), wherein the at least one circumferential tab (28) and the at least one entry segment (36) are so oriented in their angular orientation in the respective linkage area (22 or, as the case may be, 24), that these come into registry with each other in the spread open position of the pliers parts (10, 12), and wherein the at least one circumferential tab (28) can be introduced into and removed from the circumferential groove (34) through the entry segment (36) while in the other spread positions of the pliers parts (10, 12) the at least one circumferential tab (28) engages in the circumferential groove (34) and is held form-fittingly axially therein.

Advantageous embodiments of the invention are set forth in the dependent claims.

In the inventive pliers the linkage is comprised by a journal formed on one of the pliers parts and a corresponding bore formed in the other pliers part. The journal is introduced into the bore and forms the pivot linkage, whereby the cylindrical journal is guided in the cylindrical bore having the same diameter. The bore has a circumferential groove in its wall and the journal correspondingly exhibits on its outer circumferential surface at least one circumferential lobe or tab (hereafter tab). The circumferential tab of the journal engages in the circumferential groove of the bore, whereby the journal is held axially form-fittingly in the bore and whereby the two pliers parts are connected pivotably with each. In order to be able to disassemble and reassemble the pliers, the at least one circumferential tab is formed over only an angular portion of the circumference. If the two pliers parts are so designed in their corresponding angular positions that the at least one circumferential tab in the angular area overlaps with an entry opening or edge opening leading to the circumferential groove, then the journal can be inserted into the bore or can again be removed therefrom. This angular position corresponds to the spread position of the pliers with maximal opening of the pliers mouth. If the journal is inserted in the bore, then the pliers is pivoted into its closed or, as the case may be, operating position. At this time the circumferential tab is, in its angular position, pivoted against the circumferential groove, so that the circumferential tab engages in the circumferential groove and the journal thereby is axially form-fittingly held in the bore. During the use of the pliers the pliers parts are only pivoted over a spread angle area corresponding to that necessary for opening of the pliers mouth, in which the positions the circumferential tab is not rotated out of the circumferential groove. The two pliers parts are thus reliably connected to each other for the use of the pliers. If the pliers is to be disassembled for cleaning, then the pliers parts need only be spread apart beyond their normal use pivot positions, until the at least one circumferential tab comes into the angular area of the at least one entry segment, so that the journal can now be extracted axially out of the bore and the two pliers parts can be separated from each other. Both for the disassembly as well as for the assembly of the pliers no supplemental connecting means are necessary, which would need be connected or released in laborious manner. One simple manipulation is sufficient for the disassembly as well as for the assembly, without need for additional tools.

It is apparent that for the function of the take-apart linkage the circumferential groove could also be formed in the outer circumference of the journal and the circumferential tabs on the inner surface of the bore. The design which is simpler for manufacturing is however the design of the circumferential tab on the journal and the circumferential groove in the inner wall of the bore.

In an advantageous design the bore, at its base, is a closed blind bore. Thereby neither the journal nor the bore are visible in their respective linkage outer side of the pliers parts.

Further a friction element can be provided between the surfaces of the journal and the bore which are in contact with each other. This friction element has the function of imparting a defined resistance or friction in the pivot movement of the pliers. By the selection of the material and the dimensions of the friction element or insert, a defined predetermined resistance can be produced, so that the pliers on the one hand are sufficiently easily to operate and on the other hand do not move unintentionally out of the respective pivot position. If the bore is a blind bore, then the friction insert or element is preferably in the form of a disc inserted between the base of the bore and the axial surface of the journal. Thereby an even friction effect in any rotation position and an even friction or wear of the friction insert is guaranteed.

The invention further concerns the economical manufacture of the dental pliers.

In the dental pliers produced until now, first one-piece blanks are produced as press forged parts for the pliers parts, which are then processed. This manufacturing technique is labor intensive and accordingly expensive. In accordance with the invention the pliers parts are produced of two pieces. The part of the pliers which requires a high precision, namely the pliers mouth and the linkage, are milled or machined or as the case may be turned and bored or produced by pressure injection, while the lever arms are seated onto the parts forming the jaw and the linkage. For the lever arm the requirements with regard to the material and the processing precision are not as high.

Thereby there results overall a savings in material and manufacturing costs. Besides this, it is possible to combine pliers jaws and pliers lever arms with each other in diverse manner, so that a large variety of types of pliers can be produced without requiring for each type its individual manufacturing from a blank.

BRIEF DESCRIPTION OF THE DRAWINGS

In the following the invention will be described in greater detail on the basis of the illustrative embodiment shown in the figures. There is shown.

DETAILED DESCRIPTION OF THE INVENTION

The pliers, which in the illustrative embodiment are shown as dental extraction pliers, are comprised of two pliers parts 10 and 11. The two pliers parts 10 and 11 are comprised in known manner respectively of a jaws 14 or as the case may be 16, a lever arm 18 or as the case may be 20 and a linkage area 22 or as the case may be 24, which connects the respective jaw 14 or as the case may be 16 with the respective lever arm 18 or as the case may be 20. The jaws 14 and 16 form the pliers mouth and have a design which depends upon the respective intended use of the pliers. The lever arms 18 and 20 form the pliers grip and are likewise adapted to the corresponding respective intended use of the pliers.

The two pliers parts 10 and 12 are pivotably linked with each other via a linkage, which will be explained in greater detail in the following on the basis of FIGS. 2 through 7. In the illustrative embodiment the purpose of the linkage formed as inserted linkage, in which the linkage areas 22 and 24 respectively include cutouts or recesses, into which the corresponding linkage area 22 or as the case may be 24 of the other pliers part 10 or as the case may be 12 can be introduced. It is apparent that the linkage can also be in the form of a floating linkage.

Figures 2, 3:
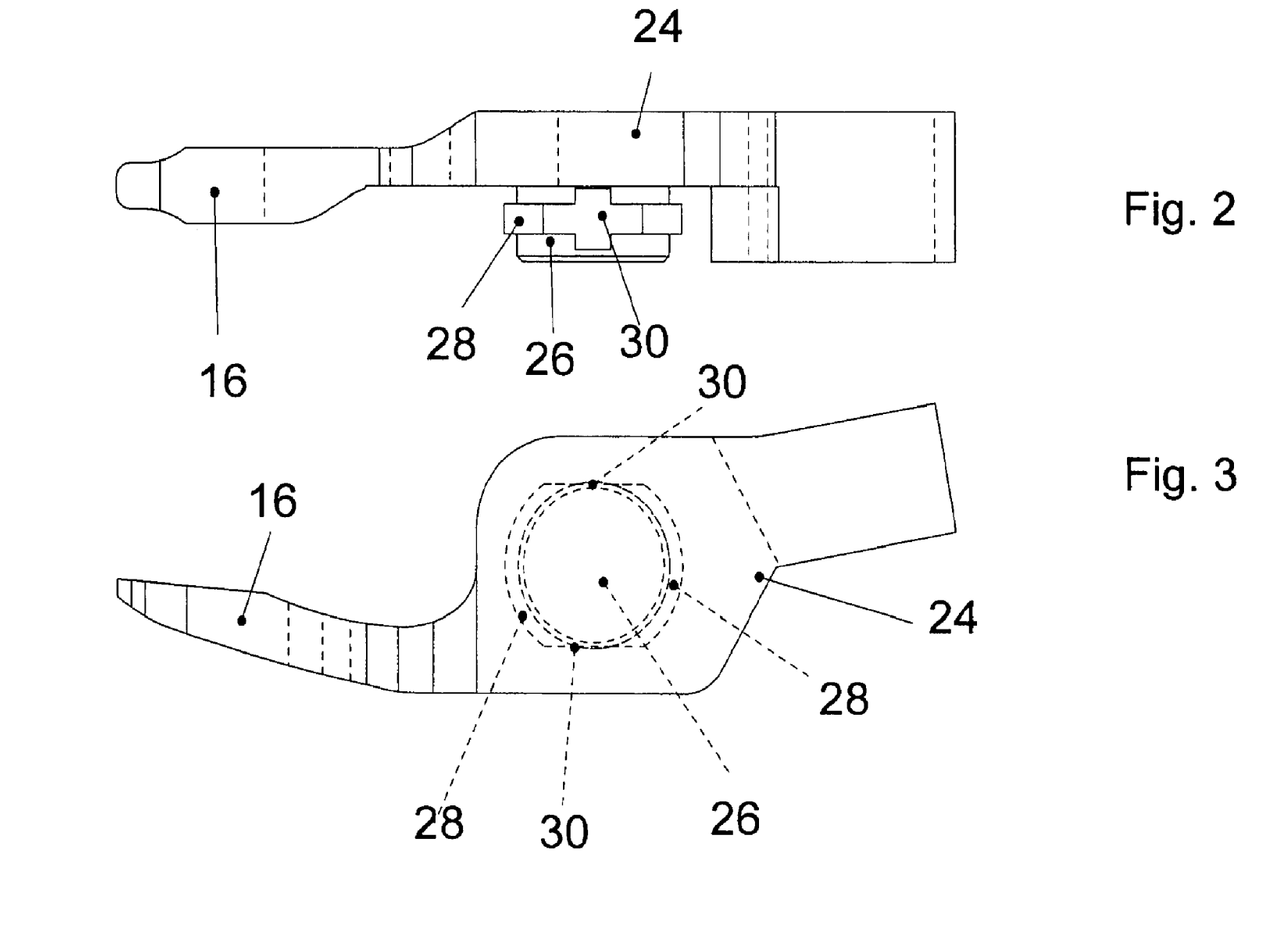

In FIGS. 2 and 3 the linkage area 24 of the second pliers part 12 is shown. On the linkage area 24 a journal 26 oriented towards the linkage area 22 of the first pliers part 10 is formed. The journal 26 has the shape of a straight cylinder, of which the central axis corresponds with the pivot axis of the pliers. At approximately half the height of the journal 26 a circumferential flange or collar 28 is formed on the outer circumference. The circumferential flange is machined away on two diametrically opposing sides, so that flat sides 30 are produced running parallel to the longitudinal direction of the pliers part 12. The machining away extends up to the diameter of the journal 26, so that the flat sides 30 are spaced apart at a distance equivalent to the diameter of the journal 26. The circumferential flange thus forms two diametrically oriented circumferential tabs 28, which extend in the longitudinal direction of the pliers part 12 in the distal or, as the case may be, proximal direction. The axial height of the journal 26 is slightly smaller than the linkage area 22 of the first pliers part 10 receiving clearance of the linkage area 24, as indicated in FIG. 2 using dash-dot lines.

Figure 4:
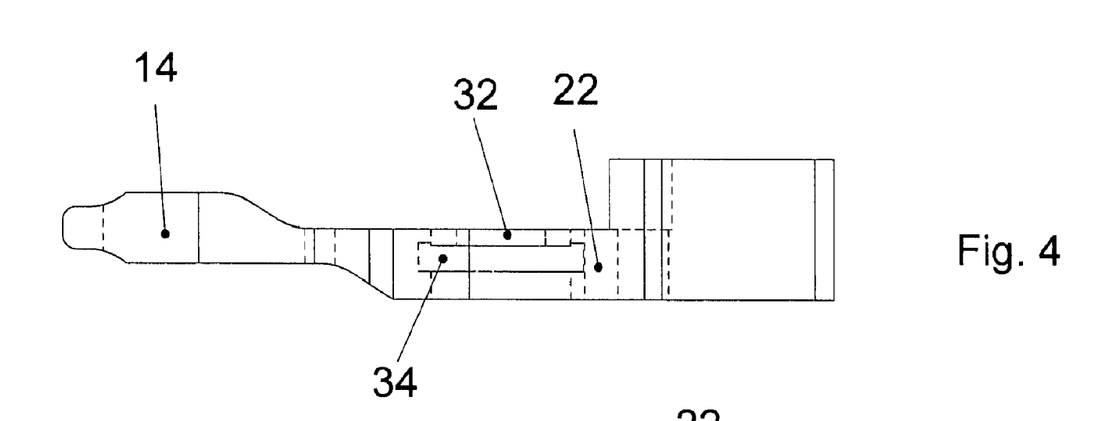
Figure 5:
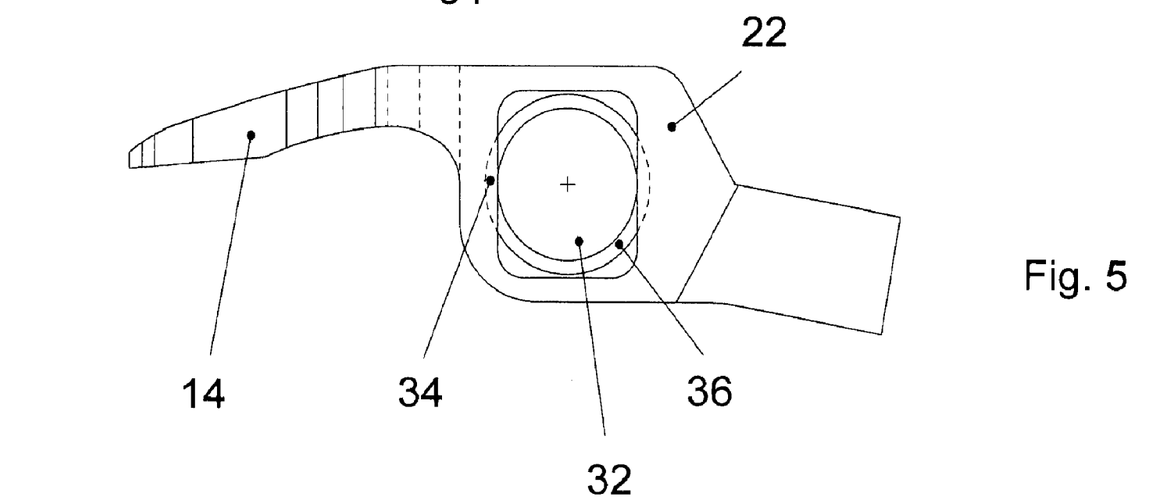

In FIGS. 4 and 5 the linkage area 22 of the first pliers part 10 is shown. This linkage area 22 exhibits a bore 32 of which the diameter corresponds to the diameter of the journal 26 and of which the center axis corresponds with the pivot axis of the pliers. The bore 32 is a blind bore, of which the axial depth is slightly larger than the axial height of the journal 26. At half the depth of the bore 32 a circumferential groove is machined into its inner circumference. The circumferential groove corresponds to the inner axial position, in its axial breadth and in its radial depth respectively to the axial position, the axial breadth and the radial height of the circumferential tabs 28 of the journal 26. On the side of the linkage area 22 facing the second pliers part 12 the diameter of the bore 32 is widened on two diametric opposing sides up to the circumferential groove 34 inwards to the outer diameter of the circumferential groove 34. Thereby two entry segments 36 are formed, which lead from the outer surface of the linkage area 22 all the way to the circumferential groove 34 and which in its cross-sectional shape and cross-sectional dimensions corresponds to the circumferential tabs or lobes 28 of the second pliers part 12. The entry segments 36 are so designed, that they are oriented perpendicular to the longitudinal direction of the pliers part 10. In order to assemble the two pliers 10 and 12, the two pliers part 10 and 12 are oriented with their longitudinal axes perpendicular to each other. Thereby the circumferential tabs 28 come into registry with their angular position with the entry segments 36. The journal 26 can now be axially introduced into the bore 32, wherein the circumferential tabs 28 enter through the entry segments 36 into the axial area of the circumferential groove 34. Now the pliers parts 10 and 12 are pivoted relative to each other into the closed position. Thereby the circumferential tabs 28 are rotated relative to the entry segments 36 and enter into the circumferential groove 34. In this position the pliers are ready for use. At this time the journal 26 is guided rotatably in the bore 32 and is held axially form-fittingly in the bore 32 by the circumferential groove 34 engaging circumferential tabs 28.

Figure 1:
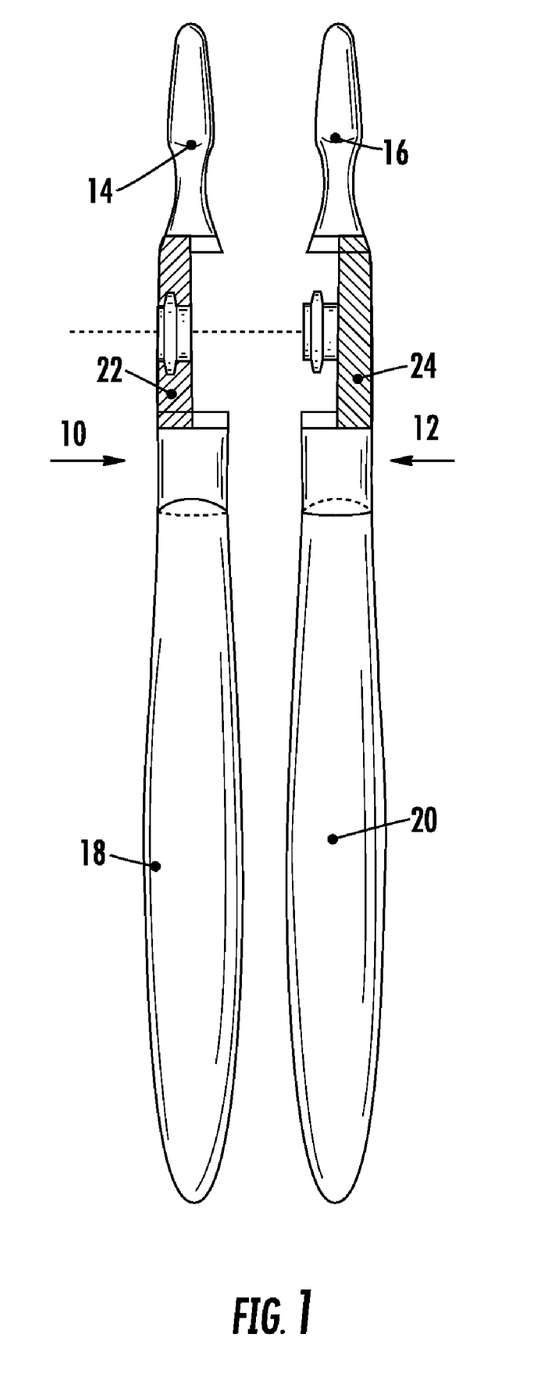
FIG. 1 an axially sectioned side view of the pliers in the area of the linkage in a first embodiment in the disassembled condition, FIG. 2 a side view of the linkage area of the first pliers part, FIG. 3 a top view upon the linkage area of the first pliers part, FIG. 4 a side view of the linkage area of the second pliers part, FIG. 5 a top view upon the linkage area of the second pliers part, FIG. 6 a side view of the linkage area of the assembled pliers, FIG. 7 a top view upon the linkage area of the assembled pliers, FIG. 8 two views of the assembled pliers in the embodiment according FIG. 1, FIG. 9 two views of the pliers in a second embodiment, FIG. 10 two views of the pliers in a third embodiment and FIG. 11 two view of the pliers in a fourth embodiment.

It is apparent that the bore 32 can also be in the form of a through-going bore, as shown in FIG. 1. The design of the bore 23 as blind bore has the advantage, that the linkage is not visible either from the outside of the linkage area 22 nor from the outside of the linkage area 24.

Figure 6:
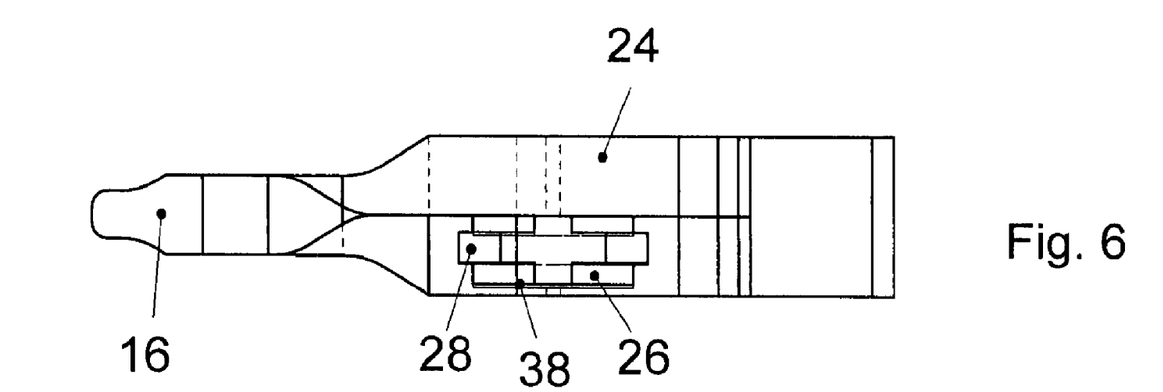
Figure 7:
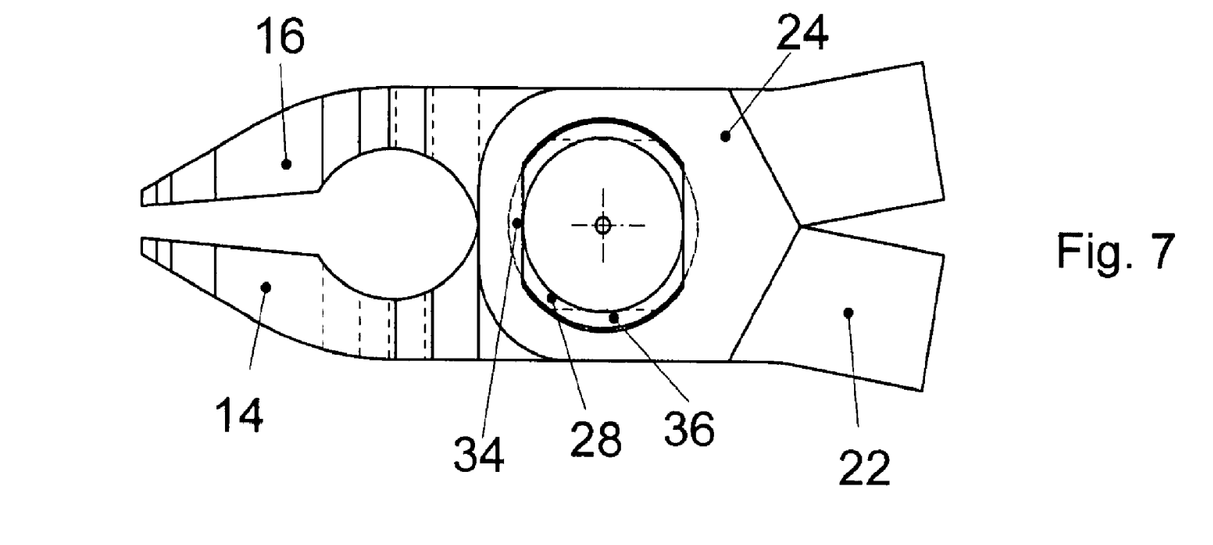

In order to be able to open and close the pliers easily and nevertheless to prevent an unintended pivoting of the pliers part 10 and 12 relative to each other, it is advantageous to introduce a friction insert 38 into the linkage. The friction insert 38 can be of any suitable material, for example plastic, which exhibits a defined elasticity and slidability in conjunction with the metal of the linkage area 22 or as the case may be 24. The friction insert 38 can be introduced for example on the axial end surface of the circumferential groove 34 so that the friction effect occurs with the circumferential tabs 28 of the journal. If the bore 32 is a blind bore, as shown in FIGS. 2 through 7, then the friction insert 38 is preferably a circular disc at the base of the bore 32, so that the friction effect occurs with the axial end surface of the journal 26, as indicated in FIG. 6. By the selection of the material and the thickness of the friction insert 38 the ease of manipulability or as the case may be the friction effect can be predicted with certainty.

It is readily apparent that the circumferential tabs 28 and the entry segments 36 need not have the shape illustrated in the figures. In place of two diametric opposing circumferential tabs 28 it would be possible to have a single radial projecting circumferential tab, in which case correspondingly only one entry segment 36 need be provided. Here also the design of the circumferential tab 38 and the entry segment 36 are so designed, that the cross-sectional surface of the circumferential tab 28 comes into registry with a cross-sectional surface of the entry segment 36 in the case that the pliers part 10 and 12 are oriented corresponding to a maximal opening or spreading of the pliers. In any other pivot position, the circumferential tab 28 engages in the circumferential groove 34, so that the journal 26 is held axially form-fittingly in the bore 32 and therewith the pliers parts 10 and 12 are pivotably connected with each other.

The jaw 14 together with the linkage area 22 and the jaw 16 together with the linkage area 24 are respectively produced as a one-piece part of a suitable metal, in particular a suitable steel. These parts may be produced by milling, turning or boring. The employed material and the manufacturing process produce an optimal precision and sturdiness in the parts essential for the use of the pliers, namely, the pliers mouth and the linkage.

The lever arms 18 and 20 are produced as separate workpieces. The lever arms 18 and 20 are sturdily connected with the respective linkage areas 22 or as the case may be 24. For this, the lever arms 18 and 20 can be mortised, welded or adhered. Since there is no urgent requirement with regard to precision and material characteristics in the grip part formed by the lever arms 18 and 20, the selection of the material and the manufacturing process for the lever arms 18 and 20 can be selected taking into consideration economical manufacturing costs.

Figure 8:
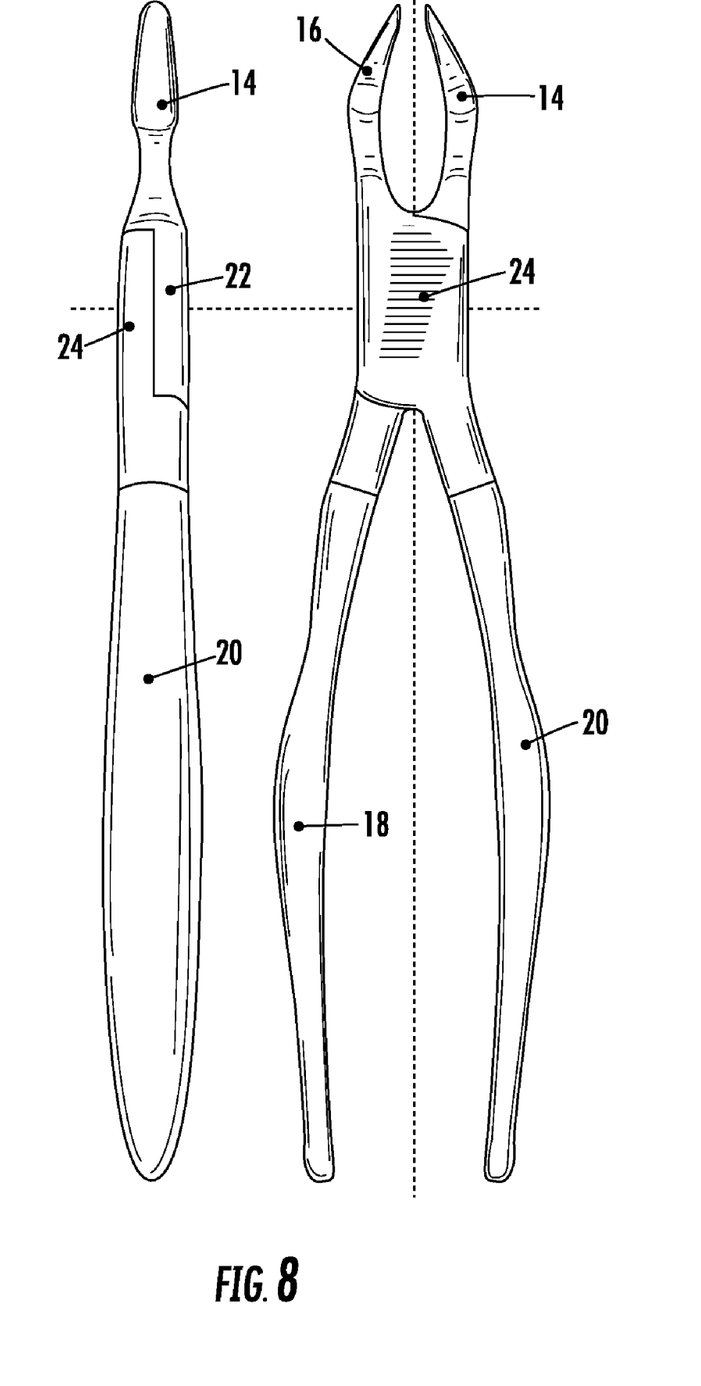
Figure 9:
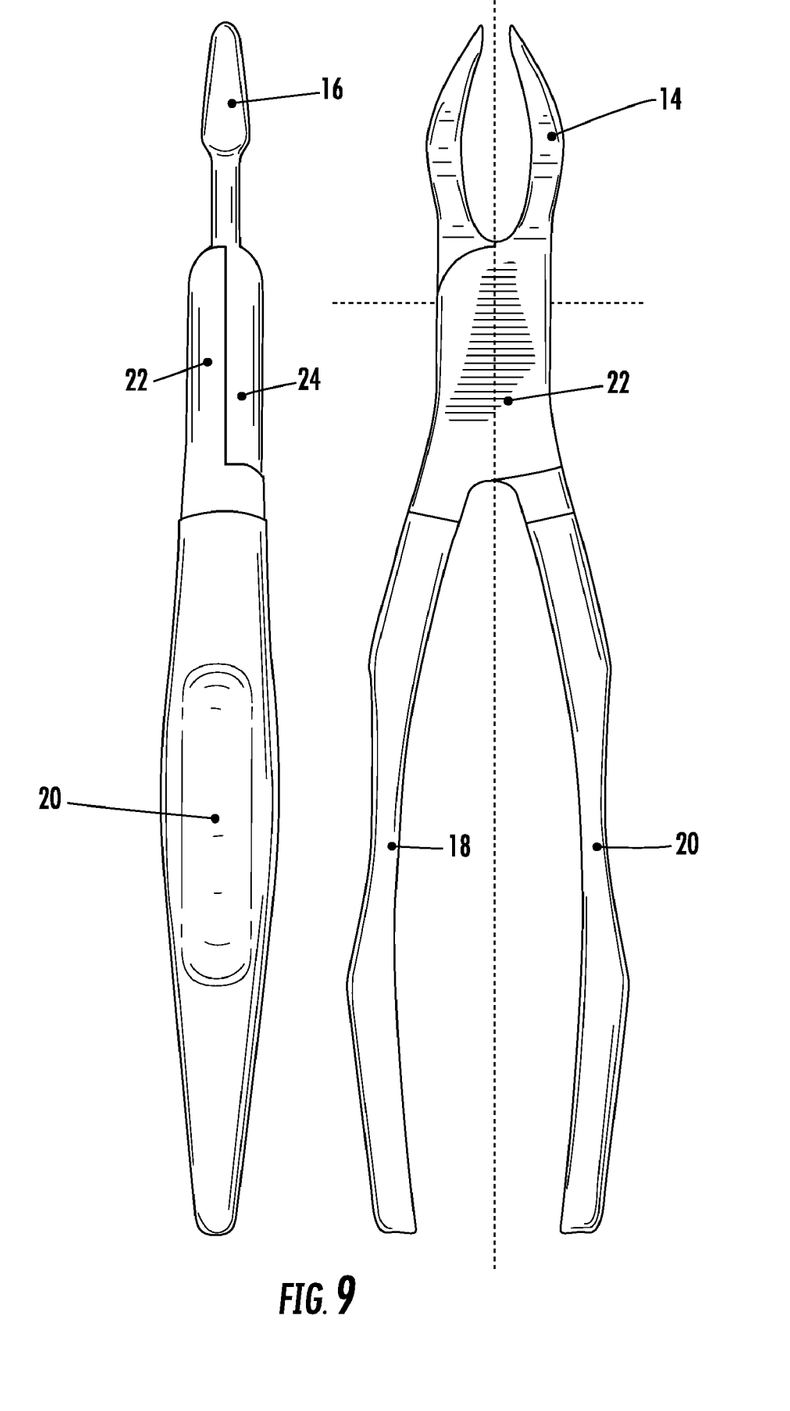
Figure 10:
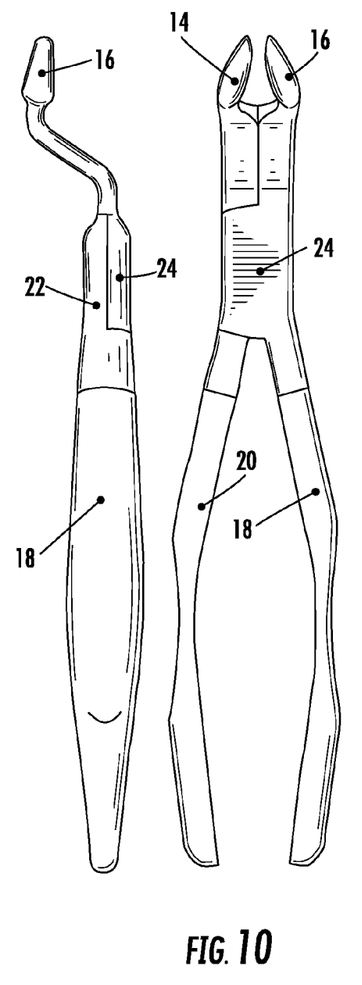
Figure 11:
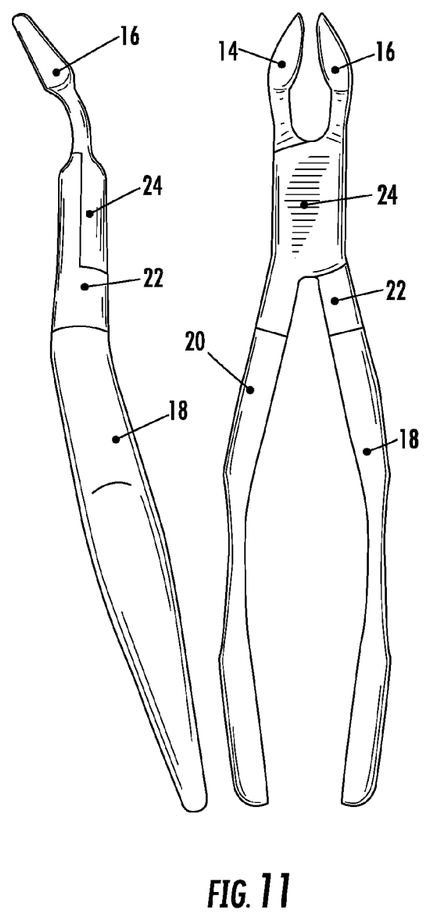

Further, the manufacture of the jaws 14 or as the case may be 16 and the linkage areas 22 or as the case may be 24 on the one hand and the lever arms 18 or as the case may be 20 on the other hand as separate workpieces has the advantage, that pliers mouth and grip shape can be combined in various manners with each other. This is exemplified using FIGS. 8 through 11. FIG. 8 shows the embodiment of the pliers represented in FIG. 1. FIG. 9 shows a pliers with the same jaws as the pliers of FIG. 8, the lever arms 18 and 20 are however of different design. FIG. 10 shows a pliers with offset pliers mouth, which are combined with lever arms 18 and 20, which correspond to the lever arms 18 and 20 of the embodiment of FIG. 9. FIG. 11 shows a pliers with an angled pliers jaws and a further angled embodiment of the lever arms 18 and 20. It can be readily seen that various other combinations of pliers mouth and pliers grip can be produced.

REFERENCE NUMBER LIST 10 first pliers part
12 second pliers part
14 jaw of 10
16 jaw of 12
18 lever arm of 10
20 lever arm of 12
22 linkage area of 10
24 linkage area of 12
26 journal
28 circumferential tab
30 flat sides
32 bore
34 circumferential groove
36 entry segment
38 friction element

The invention claimed is:

1. Dental pliers, comprising:
   a first pliers part;
   a second pliers part, the first pliers part pivotably coupleable to the second pliers part about an axis;
   a cylindrical journal (26) on the first pliers part (12) coaxial to the pivot axis;
   at least one circumferential tab (28) provided on the journal (26), the at least one circumferential tab (28) extending only over a partial angular area of the cylindrical journal's (26) circumference;
   a cylindrical bore (32) in the second pliers part (10) coaxial to the pivot axis and dimensioned to receive the cylindrical journal (26);
   at least one circumferential groove (34) in the second pliers part (10),
   at least one entry segment (36) provided in the second pliers part (10) and having a cross-sectional shape of the circumferential tab (28) and leading axially to the circumferential groove (34),
   wherein the first pliers part pivotably couples to the second pliers part by introducing the at least one circumferential tab (28) into the circumferential groove (34) through the entry segment (36) and the at least one circumferential tab (28) engages in the circumferential groove (34) and is held form-fittingly therein, and
   wherein the at least one circumferential tab (28) and the at least one circumferential groove (34) are located at a midline of the cylindrical journal (26) and at a midline of the cylindrical bore (32); and
   wherein the midline of the cylindrical journal (26) and the midline of the cylindrical bore (32) coincide and the cylindrical journal (26) is symmetric about the midline.

2. The dental pliers according to claim 1, wherein the pivotably coupling of the first pliers part to the second pliers part is an inlaid coupling.

3. The dental pliers according to claim 1, further comprising a friction element (38) at an axial end surface of the circumferential groove (34).

4. The dental pliers according to claim 1, wherein the angular positions of the at least one circumferential tab (28) and the at least one entry segment (36) are so oriented that these come into registry when the pliers parts (10, 12) are positioned at a maximal opening angle of approximately 90°.

5. The dental pliers according to claim 1, wherein two circumferential tabs (28) are arranged diametrically opposed and wherein two entry segments (36) are arranged diametrically opposed.

6. The dental pliers according to claim 1, wherein the cylindrical bore (32) extends through the second pliers part.

7. The dental pliers according to claim 1, wherein the cylindrical bore (32) is a blind bore closed at its base.

8. The dental pliers according to claim 1, wherein a friction element (38) is provided between a wall of the cylindrical bore (32) and a wall of the cylindrical journal (26).

9. The dental pliers according to claim 8, wherein the friction element (38) is provided between a base of the cylindrical bore (32) and an axial end surface of the cylindrical journal (26).

10. The dental pliers according to claim 1,
wherein the first pliers part is formed by mortising, welding or adhering a jaw of a pliers mouth and a lever arm of a pliers grip to each other.

11. The dental pliers according to claim 10, wherein the jaw and lever arm are produced from different materials.

12. The dental pliers according to claim 1, wherein a portion of the first pliers part is produced by milling, turning or boring or pressure injection.

13. The dental pliers according to claim 1, wherein the circumferential tab (28) is offset from an interface between the first and second pliers parts by a portion of the cylindrical journal (26) having a smaller diameter than a diameter of the circumferential tab (28).

14. The dental pliers according to claim 1, wherein the circumferential tab (28) include side walls providing radial-only sliding surfaces and the cylindrical journal (26) providing the axial-only sliding surfaces.

15. The dental pliers according to claim 1,
wherein the second pliers part is formed by mortising, welding or adhering a jaw of a pliers mouth and a lever arm of a pliers grip to each other.

16. The dental pliers according to claim 1, wherein the a portion of the second pliers part is produced by milling, turning or boring or pressure injection.

17. Dental pliers, comprising:
a first pliers part;
a second pliers part, the first pliers part pivotably coupleable to the second pliers part about an axis;
a cylindrical journal (26) on the first pliers part (12) coaxial to the pivot axis;
at least one circumferential tab (28) provided on the journal (26), the at least one circumferential tab (28) extending only over a partial angular area of the cylindrical journal's (26) circumference;
a cylindrical bore (32) in the second pliers part (10) coaxial to the pivot axis and dimensioned to receive the cylindrical journal (26);
at least one circumferential groove (34) in the second pliers part (10),
at least one entry segment (36) provided in the second pliers part (10) and having a cross-sectional shape of the circumferential tab (28) and leading axially to the circumferential groove (34), and
wherein the at least one circumferential tab (28) is formed on an outer circumference of the cylindrical journal (26) at approximately half height of the cylindrical journal (26);
wherein the circumferential groove (34) is formed at half depth of the cylindrical bore (32);
wherein the cylindrical journal (26) and the cylindrical bore (32) are symmetric about an intersection line at approximately half the height of the journal and half the depth of the cylindrical bore (32).

18. The dental pliers according to claim 17, wherein the at least one circumferential tab (28) and the circumferential groove (34) are located at a midline of the cylindrical journal (26) and the cylindrical bore (32).

19. The dental pliers according to claim 17, further comprising a friction element (38) at an axial end surface of the circumferential groove (34).

20. The dental pliers according to claim 17, wherein two circumferential tabs (28) are arranged diametrically opposed and wherein two entry segments (36) are arranged diametrically opposed.

* * * * *